United States Patent [19]
Sabb et al.

[11] Patent Number: 5,723,468
[45] Date of Patent: Mar. 3, 1998

[54] 6-MEMBERED RING FUSED IMIDAZOLES AS MUSCARINIC AGENTS

[75] Inventors: Annmarie Louise Sabb, Pennington, N.J.; Michael Byron Webb, Levittown, Pa.

[73] Assignee: American Home Products Corporation, Madison, N.J.

[21] Appl. No.: 728,185

[22] Filed: Oct. 1, 1996

Related U.S. Application Data

[60] Provisional application No. 60/005,065, Oct. 3, 1995.
[51] Int. Cl.[6] .................. A61K 31/52; C07D 519/00; C07D 473/00
[52] U.S. Cl. .................. 514/262; 514/266; 544/276; 544/277
[58] Field of Search .................. 544/276, 277; 514/262, 266

[56] References Cited

U.S. PATENT DOCUMENTS 5,081,253   1/1992   Santilli .................. 546/118
5,571,819  11/1996   Sabb .................. 544/265

OTHER PUBLICATIONS

Temple, Jr., J Med Chem 11, 1213 (1968).
Fukuda et al., TIPS 4–10, Dec. 1989 Supplement.
T. I. Bonner, TIPS 11–15, Dec. 1989 Supplement.
T. T. Soncrant et al., Psychopharmacology 112, 421–427 (1993).
M. Williams, Curr. Opin. Invest. Drugs 2(5), 541–544 (May 1993).
R. T. Bartus et al., Science 217, 408–417 (Jul., 1982).

Drugs of the Future 18(5), 433–435 (1992).

*Primary Examiner*—Mark L. Berch
*Attorney, Agent, or Firm*—R. F. Boswell, Jr.

[57] ABSTRACT

The compound of the formula:

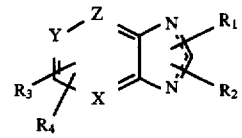

where $R_1$ is H, alkyl, perhaloalkyl, arylalkyl, alkenyl or alkynyl; $R_2$ is H when $R_4$ is other than H, and, when $R_4$ is H, $R_2$ is

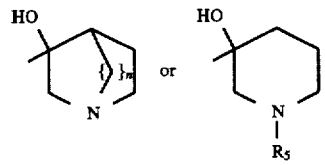

in which $R_5$ is hydrogen or alkyl; $R_3$ is hydrogen or halogen; $R_4$ is H or

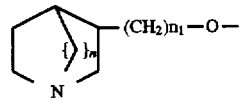

X and Y are nitrogen and Z is carbon; n is 1 or 2; $n_1$ is 0, 1, 2, 3, 4, or 5; or a pharmaceutically acceptable salt thereof are centrally active muscarinic agents.

8 Claims, No Drawings

6-MEMBERED RING FUSED IMIDAZOLES AS MUSCARINIC AGENTS

This application claims benefit of U.S. provisional application 60/005065 filed Oct. 3, 1995.

BACKGROUND OF THE INVENTION

Cognitive disorders have many components including forgetfulness, confusion, memory loss, attentional deficits, and deficits in visual perception. Some of the symptoms of cognitive disorders are associated with decreased levels of the neurotransmitter, acetylcholine. Neurological illnesses related to cholinergic deficiency include presenile dementia and senile dementia of the Alzheimer's type (SDAT), Parkinson's disease, Downe's Syndrome, and dementia pugilistica.

The "cholinergic hypothesis" [R. T. Bartus, et al., Science, 217, 408–417 (Jul. 30, 1982)] suggests that memory loss due to decreased levels of acetylcholine can be ameliorated by correcting the levels of acetylcholine in the brain using an acetylcholine releasing agent, an acetylcholine esterase inhibitor, or by using a drug which mimics acetylcholine (cholinomimetic). Marketing of the acetylcholine esterase inhibitor, tacrine, has demonstrated that improvement in memory can be shown in patients with mild to moderate Alzheimer's Disease [M. Williams, Curr. Opin. Invest. Drugs, 2(5), 541–544 (May 1993)]. The utility of this drug is limited, however, because of adverse side effects especially at the higher doses where it is most effective. Clinical studies using the natural alkaloid, arecoline, a cholinergic agonist, have also demonstrated memory improvement in patients with mild to moderate Alzheimer's Disease. Because of the short half-life of arecoline, the clinical study was done using continuous infusion of the drug over a 2 week period. In addition, a peripheral muscarinic antagonist, N-methylscopolamine, was also administered during the study to prevent potential autonomic side effects. [T. T. Soncrant et al., Psychopharmacology, 112, 421–427 (1993)].

Cholinergic receptors which bind to and are activated by the alkaloid, muscarine, are called muscarinic receptors. Three pharmacologically defined subtypes of muscarinic receptors have been identified. They are referred to as M1, M2, and M3 based upon their affinity for the M1 antagonist, pirenzepine, the M2 antagonist, AFDX-116, and the M3 antagonist, 4-[(diphenylacetyl)oxy]-1,1-dimethylpiperidinium iodide (4-DAMP). Five different human muscarinic receptors have been cloned. The Hm1 (human m1) receptor is found primarily in the frontal cortex. [T. I. Bonner, Trends in Pharmacological Sciences, supplement, Jul. 20–27 (1989) p11–15,]. Activation of the m1 receptor results in an increase in phosphoinsoitide hydrolysis (PI turnover).[K. Fukuda, et al., Ibid., p. 4–10].

U.S. Pat. No. 5,081,253 discloses a group of imidazo[4,5-c]pyridines as antiosteoporotic agents. Drugs of the Future, 18(5), 433–435 (1993) discloses a group of bicyclo (2.2.1)heptanyl substituted imidoazopyridines as adenosine $A_1$ antagonists.

DESCRIPTION OF THE INVENTION

In accordance with this invention there is provided a group of 6-membered ring fused imidazole compounds containing azacylic or azabicyclic substituents which bind to and stimulate central muscarinic acetylcholine receptors to increase cerebral acetylcholine production or release. These compounds are useful agents for treating symptoms of cognitive disorders, specifically the impaired memory associated with a decrease in the neurotransmitter, acetylcholine. The compounds of the present invention are characterized by the general formula

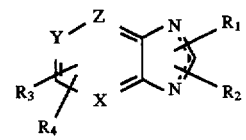

where $R_1$ is H, alkyl of 1 to 6 carbon atoms, perhaloalkyl of 1 to 6 carbon atoms, arylalkyl of 7 to 12 carbon atoms, alkenyl of 2 to 6 carbon atoms, or alkynyl of 2 to 6 carbon atoms;

$R_2$ is H when $R_4$ is other than H, and, when $R_4$ is H, $R_2$ is

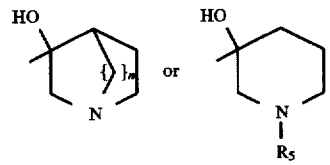

in which $R_5$ is hydrogen or alkyl of 1 to 6 carbon atoms;

$R_3$ is hydrogen or halogen;

$R_4$ is H or

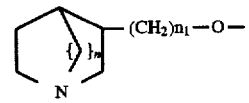

X, Y and Z are, independently, nitrogen or carbon, at least one of X, Y or Z being nitrogen;

n is 1 or 2;

$n_1$ is 0, 1, 2, 3, 4, or 5;

or a pharmaceutically acceptable salt thereof.

The pharmaceutically acceptable salts are those derived from such organic and inorganic acids as: acetic, lactic, citric, fumaric, tartaric, succinic, maleic, malonic, hydrochloric, hydrobromic, phosphoric, nitric, sulfuric, methanesulfonic, methylbenzene sulfonic, and similarly known acceptable acids.

Compounds in which n is 1 can exist as endo or exo racemates or enantiomers. Compounds in which n is 2 can be racemates or enantiomers. These stereo and optical isomers may be isolated by conventional means. The compounds of the present invention are prepared by the general synthetic methods detailed in Scheme I and Scheme II.

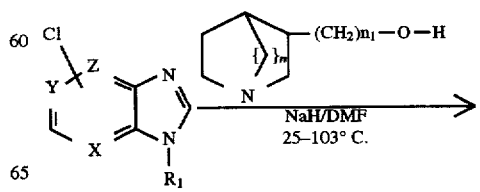

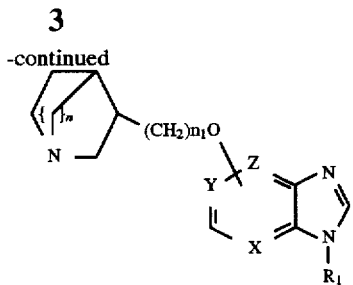

where X, Y, Z and $R_1$ are as described above.

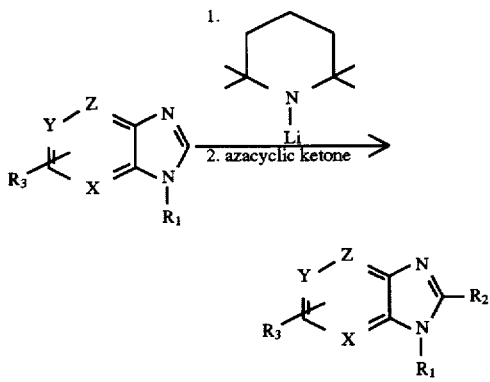

where X, Y, Z and $R_1$, $R_2$ and $R_3$ are as described above.

Referring to Scheme I, the requisite 3-hydroxy azabicyclic starting material is allowed to react with an appropriate 6-membered ring fused imidazole in an organic solvent, such as N,N-dimethylformamide (DMF) in the presence of a base, such as sodium hydride at temperatures of from 25° to 125° C. to give products of the present invention. Or referring to Scheme II, the requisite 6 membered ring fused imidazole is allowed to react with a base, such as lithium 2,2,5,5-tetramethylpiperidinamide, in an organic solvent, such as tetrahydrofuran (THF), at temperatures of from −5° to −80° C., and then the appropriate 3-keto azacyclic or azabicyclic compound in an organic solvent, such as THF, is added and stirred overnight to give products of this invention.

The following examples are presented for illustrative purposes only and are not to be construed as limitations for the disclosed invention. Those skilled in the art will be aware of other methods of preparing compounds of this invention. The starting materials or intermediates are available commercially or can be prepared by standard literature procedures.

EXAMPLE 1 endo-4-(1-Aza-bicyclo[2.2.1]hept-3-yloxy)-1-methyl-1H-imidazol[4,5-c]pyridine

4-Methoxy-3-nitropyridine (8.17 g, 53.0 mmol) was transferred to a bomb in EtOH (5–10 mL). To this was added a solution of methylamine in EtOH (26.4 mL, 8.03M, 0.212 mol). The bomb was sealed and lowered into an oil bath at 120° C. The bath temperature fell to 90° C. and remained that way for 2 hours. The temperature was raised to 140° C. over 0.5 hour and held there 0.5 hour. The contents were transferred to a flask with EtOH (not very soluble) and the solvent was evaporated. Flash chromatography on silica gel with a gradient of $CH_2Cl_2/CH_3OH$ gave 7.17 g (88%) of 4-methylamino-3-nitropyridine as a yellow solid: mp 155°–158° C.

4-Methylamino-3-nitropyridine (7.17 g, 46.8 mmol) was reductively chlorinated with $SnCl_2.2H_2O$ (42.26 g, 0.187 mol) according to the procedure described by Houston et al., J. Med. Chem. 28, 467–471 (1985), with the following modifications. The reaction was worked up by evaporation of the reaction mixture, addition of water (approximately 650 mL) with heating to dissolve most of the solid. The suspension was cooled in an ice bath and 2M ammonium hydroxide solution was added. When the precipitate persisted, additional 2M ammonium hydroxide (134 mL) was added. This mixture (pH 6) was stored overnight in the refrigerator. The solid was removed by filtration and washed with $H_2O$ (1.35 L). Evaporation of the combined filtrate and wash gave 63 g of residue. An additional water wash (500 mL) of the solid gave another 2 g of residue. Most of this solid was $NH_4Cl$. An excess of Amberlite IRA-400(OH) ion exchange resin was stirred in $CH_3OH$ and the residue from the evaporation was added. After stirring for 0.5 to 1 hour, the solvent was removed by evaporation under reduced pressure and the residue was azeotroped with absolute EtOH two times to give 5.94 g (81%) of 3-amino-2-chloro-4-methylaminopyridine as an oil which was one spot by TLC (silica gel, 1:9 MeOH: $CH_2Cl_2$); $^1H$ NMR (200 MHz, DMSO-$d_6$) δ7.41 (1H, d, J=6.6 Hz), 6.34 (1H, d, J=6.6 Hz), 5.88 (1H, poorly resolved quartet), 4.67 (2H, s), 2.74 (3H, d, J=5.3 Hz).

To a heterogeneous mixture of 3-amino-2-chloro-4-methylaminopyridine (5.9 g, 37 mmol) and triethyl orthoformate (12.92 mL, 87.2 mmol) was added 5 drops of conc. $H_2SO_4$. A short path distillation apparatus was attached. The reaction flask was lowered into a hot oil bath and stirred at 110° C. to 190° C. The time spent heating was 20–25 minutes. On cooling, the thick residue was dissolved in $CH_2Cl_2$ (40 mL) and was allowed to stir overnight with a little CaO. The solid was removed by filtration and the filtrate was concentrated. Flash chromatography on silica gel eluting with ($CH_2Cl_2/CH_3OH$, 95:5) gave 5.65 g (91%) of 4-chloro-1-methyl-1H-imidazo[4,5-c]pyridine as a light yellow solid: mp 127°–131° C.; MS 167 ($M^+$).

To a stirred suspension of 60% NaH/oil (0.14 g, 5.8 mmol, washed with hexane) in DMF (40 mL) was added endo-1-azabicyclo[2.2.1]heptan-3-ol (0.50 g, 4.4 mmol) at room temperature. The reaction mixture was stirred at 87° C. for 1 hour. 4-Chloro-1-methyl-1H-imidazo[4,5-c]pyridine (0.70 g, 4.2 mmol) was added and the temperature was raised to 103° C. for 2–3 hours and then stirred at room temperature overnight. The DMF was rotary evaporated under high vacuum and the residue was loaded on a column of basic alumina, activity 1, and eluted with a gradient of EtOAc/$CH_3OH$ to give 0.42 g of the free base of the title compound as a light brown oil. The HCl salt was prepared in ETOH with HCl sat. $Et_2O$. The solid was filtered and dried at 40° C./25 mm pressure to give 0.35 g (26%) of the dihydrochloride of the title compound as a hygroscopic white powder: mp 230°–234° C.

Elemental analysis for: $C_{13}H_{16}N_4O.2HCl$: Calc'd: C, 49.22; H, 5.72; N, 17.66 Found: C, 49.11; H, 5.65; N, 17.64

EXAMPLE 2

(+)-endo-4-(1-Aza-bicyclo[2.2.1]hept-3yloxy)-1-methyl-1H-imidazo-[4,5-c]pyridine The compound produced in Example 1 (1.19 g) was resolved using a Chiralpak AS column (25×0.46 cm) and eluting with (Hexane:EtOAc, 85:15 with a trace of triethylamine (TEA), 0.75 mL/min.) The first compound eluted from the column (0.49 g) was treated with ethereal HCl in ethanol to give 0.45 g (59% from the racemic base) of the title compound as the dihydrochloride: mp 235°–237° C.; $[\alpha]_D$=3.61 (c 10.8, $CH_3OH$).

Elemental analysis for: $C_{13}H_{16}N_4O.2HCl$: Calc'd: C, 49.22; H, 5.72; N, 17.66 Found: C, 48.85; H, 5.68; N,. 17.82

EXAMPLE 3

(−)-endo-4-(1-Aza-bicyclo[2.2.1]hept-3-yloxy)-1methyl-1H-imidazol[4,5-c]pyridine The compound produced in Example 1 (1.19 g) was resolved using a Chiralpak AS column (25×0.46 cm) and eluting with (Hexane:EtOAc, 85:15 with a trace of triethylamine (TEA), 0.75 mL/min.) The second compound eluted from the column (0.33 g) was treated with ethereal HCl in ethanol to give 0.20 g (26% from the racemic base) of the title compound as the dihydrochloride: mp 234°–238° C.; $[\alpha]_D$=−2.45 (c 13.8, $CH_3OH$).

Elemental analysis for: $C_{13}H_{16}N_4O.2HCl$ Calc'd: C, 49.22; H, 5.72; N, 17.66 Found: C, 49.54; H, 5.67; N, 17.40

EXAMPLE 4

(exo)-4-(1-Aza-bicyclo[2.2.1]hept-3-yloxy)-1-methyl-1H-imidazo[4,5-c]pyridine

Following the procedure of Example 1, 4-chloro-1-methyl-1H-imidazo[4,5-c]pyridine (0.70 g, 4.2 mmol) was treated with exo-azabicyclo[2.2.1]heptan-3-ol (0.50 g, 4.4 mmol) to give the free base of the title compound which was converted with ethereal HCl to 0.68 g (54%) of the mono hydrate, hydrochloride salt: (hygroscopic).

Elemental analysis for: $C_{13}H_{15}N_4O.HCl.H_2O$ Calc'd: C, 51.84; H, 5.88; N, 18.60 Found: C, 51.86; H, 6.02, N; 18.37

EXAMPLE 5

3-(1-Benzyl-1H-imidazo[4,5-c]pyridin-4-yloxy)-1-aza-bicyclo[2.2.2]octane

4-Methoxy-3-nitropyridine hydrochloride (10.32 g, 54.15 mmol) was treated with an excess of Amberlite IRA-400 (OH) ion-exchange resin in methanol. Filtration and evaporation of the filtrate gave the free base (8.09 g, 52.5 mmol). This was dissolved in benzylamine (32 ml, 31 g, 0.29 mol). The solution was lowered into an oil bath and stirred at 120°–140° C. for 50 minutes. The excess amine was evaporated. The oil crystallized and was nearly pure on TLC ($CH_2Cl_2/CH_3OH$, 9/1). Some benzylamine was present. The solid was crushed. $H_2O$ was added. The mixture was stirred for 1 hour. Filtration of the solid and drying at 40° C. under 25 mm pressure overnight gave 11.46 g (92%) of 4-benzylamino-3-nitropyridine: mp 100°–104° C.

4-Benzylamino-3-nitropyridine (11.4 g, 49.7 mmol) was reductively chlorinated with $SnCl_2.2H_2O$ (51.67 g, 0.229 mol) according to the procedure described by Houston et al., loc. cit., with the following modifications. The reaction was worked up by evaporation of the reaction mixture. Water (approximately 650 mL) was added to the residue and heated to dissolve the solid. Some solid remained and was ignored. The solution was cooled in an ice bath as aqueous 2M $NH_3$ was added. When the precipitate persisted, additional aqueous 2M $NH_3$ (134 mL) was added. This mixture (pH=6) was stored overnight in the refrigerator. The solid was removed by filtration and washed with $H_2O$ (1.35 L). Evaporation of the combined filtrate and wash gave 63 g of residue. An additional wash ($H_2O$, 500 mL) of the solid gave another 2 g of residue. Most of this solid was $NH_4Cl$. Amberlite IRA-400(OH) ion exchange resin (350 mL of solid, approximately half of what was needed) was stirred in $CH_3OH$ and the residue from the evaporation was added, stirred 0.5–1 hour, filtered and evaporated. Absolute EtOH was added and evaporated to remove $H_2O$, then repeated once more to give 24.19 g of solid. Most of this was probably still $NH_4Cl$. This was stirred with a minimum of $CH_2Cl_2/CH_3OH$, 9/1. The heterogeneous mixture was loaded on a silica gel column. Elution with the same solvent gave, nearly pure on TLC ($CH_2Cl_2/CH_3OH$, 9/1), 5.78 g, (50%) of 3-amino-4-benzylamino-2-chloropyridine, mp 176°–179° C.

To a heterogeneous mixture of 3-amino-4-benzylamino-2-chloropyridine (2.90 g, 12.0 mmol) and triethyl orthoformate (3.5 mL, 3.1 g, 21 mmol) was added 3 drops of concentrated $H_2SO_4$. A short path distillation apparatus was attached. The reaction flask was lowered into a hot oil bath and stirred at 130° C. The temperature fell to 120° C. so the heat was raised to 165° C. The time spent heating was 0.5 hour. On cooling, the thick residue was dissolved in $CH_3OH$ (less than one volume) and allowed to stir overnight with a little CaO. The solid was removed by filtration and the solution concentrated. Flash chromatography on silica gel ($CH_2Cl_2/CH_3OH$, 98/2) gave 2.27 g of oil contaminated with orthoformate by NMR. An additional 0.76 g of product was collected. Heating the first sample under high vacuum for a few minutes gave 2.14 g of 1-benzyl-4-chloro-1H-imidazo[4,5-c]pyridine. Both of the samples were thick oils: 2.90 g (96%); MS 243 ($M^+$).

Following the procedure of Example 1, 1-benzyl-4-chloro-1H-imidazo[4,5-c]pyridine (0.78 g, 3.2 mmol) was treated with 3-quinuclidinol (0.44 g, 3.5 mmol) to give 0.52 g (39%) of the title compound as the hydrochloride, 2.5 hydrate: mp 162°–183° C.

Elemental analysis for: $C_{20}H_{22}N_4O.HCl.2.5H_2$ Calc'd: C, 57.76; H, 6.79; N, 13.47 Found: C, 57.78; H, 6.69; N, 13.52.

EXAMPLE 6

(+)-3-(1-Benzyl-1H-imidazo[4,5-c]pyridin-4-yloxy)-1-aza-bicyclo[2.2.2]octane

Following the procedure of Example 2, the free base of the title compound was eluted as the first band from the chiral column and the hydrochloride salt (0.054 g) was formed (hygroscopic) to give the title compound as the dihydrochloride, 0.7 hydrate: $[\alpha]_D$=5.34 (c.5.616 mg/mL MeOH).

Elemental analysis for: $C_{20}H_{22}N_4O.2HCl.0.7 \ H_2O$ Calc'd: C, 57.20; H, 6.10; N, 13.34 Found: C, 57.21; H, 6.27; N, 13.45

EXAMPLE 7

(−)-3-(1-Benzyl-1H-imidazol[4,5-c]pyridin-4-yloxy)-1-aza-bicyclo[2.2.2]octane

Following the procedure of Example 2, the free base of the title compound was eluted as the second band from the chiral column and the dihydrochloride, 2.2 hydrate salt (0.076 g) was formed (hygroscopic): $[\alpha]_D$=−6.83 (c, 10.255 mg/mL MeOH).

Elemental analysis for: $C_{20}H_{22}N_4O.2HCl.2.2H_2O$ Calc'd: C, 58.52; H, 6.73 N, 13.65 Found: C, 58.53; H, 6.37; N, 113.80

EXAMPLE 8

3-(1-Methyl-1H-imidazo[4,5-c]pyridin-4-yloxymethyl)-1-aza-bicyclo[2.2.2]octane

Following the procedure of Example 1, 4-chloro-1-methyl-1H-imidazo[4,5-c]pyridine (0.51 g, 3.0 mmol) was treated with 3-hydroxymethyl-1-azabicyclo[2.2.2] octane and the product converted to the hydrochloride salt to give 0.38 g (33%) of the dihydrochloride, 0.9 hydrate, 0.4 ethanolate of the title compound:

Elemental analysis for: $C_{15}H_{20}N_4O \cdot 2HCl \cdot 0.4EtOH \cdot 0.9H_2O$ Calc'd: C, 49.95; H, 6.95; N, 14.74 Found: C, 49.97; H, 6.98; N, 14.68

EXAMPLE 9 endo-6-(1Aza-bicyclo[2.2.1]hept-3-yloxy)-9-methylpurine endo-3-hydroxy-1-aza-bicyclo[2.2.1]heptane (500 mg, 4.5 mmol) was dissolved in anhydrous DMF (20 mL) in a nitrogen atmosphere. Sodium hydride (180 mg from 300 mg 60% NaH in oil washed twice with hexane and decanted) was added and the mixture was stirred at room temperature for 30 minutes. 6-Chloro-9-methylpurine (750 mg, 4.5 mmol) in dry DMF (10 mL) was added and the reaction mixture was stirred for 2.5 hours and then quenched with water (120 mL) and extracted with ethyl acetate (5×100 mL). The aqueous phase was evaporated to dryness on a rotary evaporator under vacuum to give a yellow oily solid that was purified by flash chromatography through alumina eluting with 3–5% methanol in ethyl acetate to give the hemihydrate of the title compound (85 mg, 7.5%): m.p. 146°–148° C. (recrystallized from benzene/hexane).

Elemental analysis for: $C_{12}H_{15}N_5O \cdot 0.5\ H_2O$ Calc'd: C, 58.76; H, 6.16; N, 28.55. Found: C, 56.94; H, 6.34; N, 27.54

EXAMPLE 10 exo-6-(1Aza-bicyclo[2.2.1]hept-3-yloxy)-9-methylpurine

Following the procedure of Example 9, the sodium salt of exo-3-hydroxy-1-aza-bicyclo[2.2.1]heptane was allowed to react with 6-chloro-9-methylpurine to give the 1.6 hydrate of the title compound (13 mg, 1.1%): m.p.78°–82° C. as a white amorphous solid after chromatography through silica gel eluting with 5% methanol and 0.25% ammoium hydroxide in methylene chloride.

Elemental analysis for: $C_{12}H_{15}N_5O \cdot 1.6\ H_2O$ Calc'd: C, 52.58; H, 6.69; N, 25.55 Found: C, 52.92.; H, 6.49. N, 25.00

EXAMPLE 11 endo-6-(1Aza-bicyclo[2.2.1]hept-3-yloxy)-7-methylpurine

Following the procedure of Example 9, but substituting 6-chloro-7-methylpurine gave the title compound (65 mg, 9%) after flash chromatography on alumina eluting with 3–5% methanol in ethyl acetate followed by recrystallization from ethyl acetate and hexane: m.p. 176°–177° C.

Elemental analysis for: $C_{12}H_{15}N_5O$ Calc'd: C, 58.76; H, 6.16;. N, 28.55 Found: C, 58.92; H, 6.06; N, 28.38

EXAMPLE 12 exo-6-(1-Aza-bicyclo[2.2.1]hept-3-yloxy)-7-methylpurine

Following the procedure of Example 9, the sodium salt of exo-3-hydroxy-1-aza-bicyclo[2.2.1]heptane was allowed to react with 6-chloro-7-methylpurine to give the 0.57 hydrate of the title compound (30 mg, 3%) as a white amorphous solid (hygroscopic) after chromatography through silica gel eluting with 5% methanol and 0.25% ammoium hydroxide in methylene chloride followed by dissolving the product in methylene chloride, treating with charcoal, filtering through Celite and evaporating the solvent.

Elemental analysis for: $C_{12}H_{15}N_5O \cdot 0.57\ H_2O$ Calc'd: C, 56.40; H, 6.37; N, 27.40 Found: C, 56.76; H, 6.28; N, 27.01

EXAMPLE 13

3-(1-Methyl-1H-imidazo[4,5-b]pyridin-2-yl)-1-aza-bicyclo[2.2.2]octan-3-ol

To a solution of 2,2,5,5-tetramethylpiperidine (0.85 mL, 0.71 g, 5.0 mmol) in THF (40 mL) at −5° C. was added n-butyllithium in hexane (1.95 mL, 2.61M, 5.09 mmol) over 1 minute. The solution was stirred at −5° to −15° C. for 20 minutes and then cooled in a dry ice acetone bath. The known compound 3-methyl-3H-imidazo[4,5-b]pyridine (Chem. Abstracts, 69: 19153y) (0.50 g, 3.8 mmol) in THF (2–3 mL) was added over 1 minute. A solution of 3-quinuclidinone in THF (3.0 mL, 1.4M, 4.2 mmol, dried over 4A sieves) was added over 1 minute at −78° C. The solution was stirred and allowed to warm slowly over night. Approximately 1 mL of saturated $NH_4Cl$ was added to the green heterogeneous mixture. The solvent was evaporated. EtOH was added and evaporated to dryness. This was repeated once. The mixture was stirred with a little $CH_2Cl_2$ and $CH_3OH$. This was added to a column of basic alumina and eluted with a gradient of $CH_2Cl_2/CH_3OH$ to give 0.54 g of free base. The salt was prepared by adding an excess of HCl saturated $Et_2O$. Filtration of the salt and drying at 40° C. under 25 mm pressure gave 0.58 g (44%) of the dihydrochloride, 0.2 hydrate, 0.2 ethanolate of the title compound: dec. 265°–268° C.; MS 258 ($M^+$).

EXAMPLE 14

3-(1-Benzyl-4-chloro-1H-imidazo[4,5-c]pyridin-2-yl)-1-aza-bicyclo[2.2.2]octan-3-ol Following the procedure of Example 13 and substituting 1-benzyl-4-chloro-1H-imidazo[4,5-c]pyridine (0.73 g, 3.0 mmol) gave the free base of the title compound which was purified by flash chromatography on silica gel with a gradient of methanol in ethyl acetate. Preparation of the salt as described gave the dihydrochloride as an amorphous solid, 0.31 g (23%):

Elemental analysis for: $C_{20}H_{21}ClN_4O \cdot 2HCl$ Calc'd: C, 54.37; H, 5.25; N, 12.68 Found: C, 54.00; H, 5.09; N, 12.69

EXAMPLE 15

3-(1-Benzyl-4-chloro-1H-imidazo[4,5-c]pyridin-2-yl)-1-ethyl-piperidin-3ol

Following the procedure of Example 13 and using 1-benzyl-4-chloro-1H-imidazo[4,5-c]pyridine (0.60 g, 2.5 mmol) and (0.36 g, 2.8 mmol) of N-ethyl-3-piperidone gave the free base of the title compound which was purified by flash chromatography on silica gel eluting with EtOAc to give, after preparation of the salt, the dihydrochloride, 0.59 hydrate as an amorphous solid, 0.30 g (26%):

Elemental analysis for: $C_{20}H_{23}ClN_4O \cdot 2HCl \cdot 0.59H_2O$ Calc'd: C, 52.86; H, 5.81; N, 12.33 Found: C, 52.86; H, 5.99; N, 12.50

The affinity of the compounds of this invention for muscarinic receptors was established by testing them in accordance with the standard pharmacomogical test procedures in which the compound's ability to compete with [$^3$H]QNB binding and by analysis of PI hydrolysis stimulation in accordance with the following test procedures:

The binding affinity of the compounds of this invention at muscarinic receptor subtypes was determined by incubating triplicate samples of homogenized Chinese Hamster Ovary (CHO) cells which had been transfected with CMV vector containing cDNA expressing individual muscarinic receptor subtypes, for one hour at 37° C. with 0.23 nM radiolabeled quinuclidinyl benzilate [$^3$H]QNB, a representative compound of this invention, and a volume of 10 mM phosphate buffer to obtain a final incubation volume of 1000 µL. Vehicle and 2 µM atropine sulfate are substituted for the test solution to determine total and non-specific bindings, respectively. After incubation, the solutions are filtered and the filter paper is subjected to scintillation spectroscopy for radioactivity counting. Specific binding in the presence of the compound of this invention is expressed as a percentage of the atropine-sensitive binding. A concentration-response evaluation is obtained through non-linear regression analysis to obtain an IC$_{50}$ and/or K$_i$ value. This procedure is based on that of Tonnaer et al, Life Sci., 40, 1981 (1987).

The ability of the compounds of this invention to stimulate hydrolysis of phosphoinositide (PI) in chinese Hamster Ovary (CHO) cells which had been transfected with CMV vector containing cDNA expressing M$_1$ acetylcholine receptors was determined in accordance with the procedure of El-Fakahany et al, J. Pharmacol. Exp. Ther. 257, 938 (1991), whereby PI hydrolysis is performed in reaction tubes, each containing 880 µL Kreb's Buffer, 10 µL of 1.0M LiCl solution, 10 µL of the compound representatve of this invention or control vehicle, and 100 µL of CHO cell suspension in Kreb's Buffer (1,000,000 cells per mL). The tubes are incubated for one hour at 37° C. The reaction is quenched with chloroform and the phosphatidyl inositols are extracted with methanol and chloroform. Phase separation is assured with the addition of methanol and water followed by centrifugation. The tritiated inositol phosphates are recovered on BioRad AG 1-X8 anion exchange resin in the formate cycle. After washing the resin with water and myo-inositol, the inositol phosphates are eluted with ammonium formate/formic acid, collected and subjected to liquid scintillation spectroscopy. The results are expressed as a percentage of the mean value obtained for carbachol (EC$_{50}$= 8.0 µM).

The results of these studies are given in the Table below:

| Example | ml $^3$H QNB Binding in CHO cells K$_i$ (µM) | % PI Hydrolysis ml receptors in CHO cells 30 × K$_i$ (µM) carb = 100% | % PIHydrolysis ml receptors in CHO cells maximum % cabachol = 100% | % PI Hydrolysis ml receptors in CHO cells ED$_{50}$ |
|---|---|---|---|---|
| 1 | 19.29 | 25.0 | 21.7 | 51.8 |
| 2 | 42.7% @ 300 µM | | | |
| 3 | 14.2 | 20.6 | 26.2 | 62 |
| 4 | 20.57 | | | |
| 5 | 3.85 | 6.8 | | |
| 6 | 13.43 | | | |
| 7 | 17.65 | 18.4 | | |
| 8 | 2.65 | | | |
| 9 | 27.04 | | | |
| 10 | 17.08 | | | |
| 11 | 21.2% @ 300 µM | | | |
| 12 | 24.7% @ 300 µM | | | |
| 13 | 1.42 | | | |
| 14 | 1.65 | | | |
| 15 | 9.3 | | | |

Hence, the compounds of this invention demonstrated high affinity for muscarinic receptors (especially the ml receptor) and are therefore useful in the treatment of disease states associated with insufficient cerebral acetylcholine production or release.

Based upon this receptor binding information and PI hydrolysis, the compounds of this invention are characterized as useful in the treatment of cognitive disorders associated with decreased levels of cerebral acetylcholine production or release, such as presenile dementia, senile dementia of the Alzheimer's type, Parkinson's disease, Downe's Syndrome and dementia pugilitica.

As such, the compounds may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection.

Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific patient suffering from cerebral acetylcholine insufficiency must be subjectively determined by the attending physician. The variables involved include the severity of the dysfunction, and the size, age and response pattern of the patient.

What is claimed is:

1. A compound of the formula:

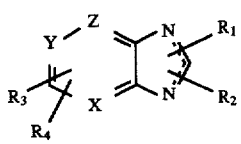

where $R_1$ is H, alkyl of 1 to 6 carbon atoms, perhaloalkyl of 1 to 6 carbon atoms, arylalkyl of 7 to 12 carbon atoms, alkenyl of 2 to 6 carbon atoms, or alkynyl of 2 to 6 carbon atoms;

$R_2$ is H when $R_4$ is other than H, and, when $R_4$ is H, $R_2$ is

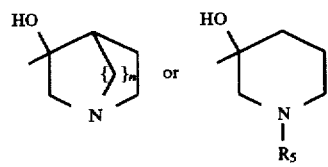

in which $R_5$ is hydrogen or alkyl of 1 to 6 carbon atoms;

$R_3$ is hydrogen or halogen;

$R_4$ is H or

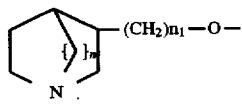

X and Y are nitrogen and Z is carbon;

n is 1 or 2;

$n_1$ is 0, 1, 2, 3, 4, or 5;

or a pharmaceutically acceptable salt thereof.

2. The compound of claim 1 which is endo-6-(1-aza-bicyclo[2.2.1]hept-3-yloxy)-9-methylpurine or a pharmaceutically acceptable salt thereof.

3. The compound of claim 1 which isexo-6-(1-aza-bicyclo[2.2.1]hept-3-yloxy)-9-methylpurine or a pharmaceutically acceptable salt thereof.

4. The compound of claim 1 which is endo-6-(1-aza-bicyclo[2.2.1]hept-3-yloxy)-7-methylpurine or a pharmaceutically acceptable salt thereof.

5. The compound of claim 1 which is exo-6-(1-aza-bicyclo[2.2.1]hept-3-yloxy)-methylpurine or a pharmaceutically acceptable salt thereof.

6. A method for alleviating the symptoms of neurological illness attending acetylcholine deficiency which comprises administering to a patient in need thereof, parenterally or orally, a muscarinic receptor active compound of the formula:

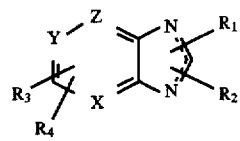

where $R_1$ is H, alkyl of 1 to 6 carbon atoms, perhaloalkyl of 1 to 6 carbon atoms, arylalkyl of 7 to 12 carbon atoms, alkenyl of 2 to 6 carbon atoms, or alkynyl of 2 to 6 carbon atoms;

$R_2$ is H when $R_4$ is other than H, and, when $R_4$ is H, $R_2$ is

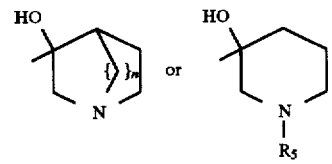

in which $R_5$ is hydrogen or alkyl of 1 to 6 carbon atoms;

$R_3$ is hydrogen or halogen;

$R_4$ is H or

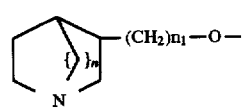

X and Y are nitrogen and Z is carbon;

n is 1 or 2;

$n_1$ is 0, 1, 2, 3, 4, or 5;

or a pharmaceutically acceptable salt thereof, in an amount sufficient to relieve the neurological symptoms of said patient.

7. A method of alleviating memory loss attending senility which comprises administering to a patient in need thereof, parenterally or orally, a muscarinic receptor active compound of the formula:

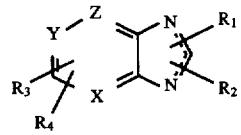

where $R_1$ is H, alkyl of 1 to 6 carbon atoms, perhaloalkyl of 1 to 6 carbon atoms, arylalkyl of 7 to 12 carbon atoms, alkenyl of 2 to 6 carbon atoms, or alkynyl of 2 to 6 carbon atoms;

$R_2$ is H when $R_4$ is other than H, and, when $R_4$ is H, $R_2$ is

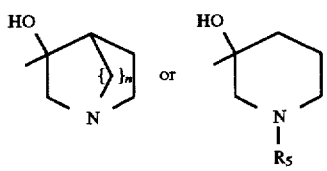

in which R$_5$ is hydrogen or alkyl of 1 to 6 carbon atoms;

R$_3$ is hydrogen or halogen;

R$_4$ is H or

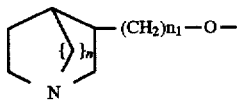

X and Y nitrogen and Z is carbon;

n is 1 or 2;

n$_1$ is 0, 1, 2, 3, 4, or 5;

or a pharmaceutically acceptable salt thereof, in an amount sufficient to enhance cognition.

8. A method for alleviating the neurological symptoms attending Parkinson's disease or senile pugilistica, which comprises administering to a patient in need thereof, parenterally or orally, a muscarinic receptor active compound of the formula:

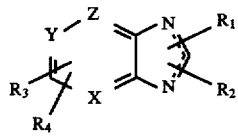

where

R$_1$ is H, alkyl of 1 to 6 carbon atoms, perhaloalkyl of 1 to 6 carbon atoms, arylalkyl of 7 to 12 carbon atoms, alkenyl of 2 to 6 carbon atoms, or alkynyl of 2 to 6 carbon atoms;

R$_2$ is H when R$_4$ is other than H, and, when R$_4$ is H, R$_2$ is

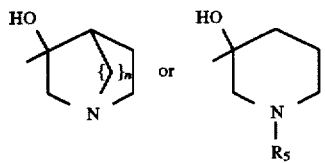

in which R$_5$ is hydrogen or alkyl of 1 to 6 carbon atoms;

R$_3$ is hydrogen or halogen;

R$_4$ is H or

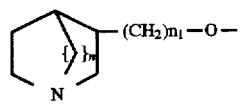

X and Y are nitrogen and Z is carbon;

n is 1 or 2;

n$_1$ is 0, 1, 2, 3, 4, or 5;

or a pharmaceutically acceptable salt thereof, in an amount sufficient to alleviate said neurological symptoms.

* * * * *